United States Patent [19]

Sugita et al.

[11] Patent Number: 5,021,532
[45] Date of Patent: Jun. 4, 1991

[54] ONE END-REACTIVE ORGANOPOLYSILOXANE COMPOUND

[75] Inventors: Toshikazu Sugita; Akinari Itagaki, both of Annaka, Japan

[73] Assignee: Shin-Etsu Chemical Co., Ltd., Tokyo, Japan

[21] Appl. No.: 407,280

[22] Filed: Sep. 14, 1989

[30] Foreign Application Priority Data

Sep. 27, 1988 [JP] Japan .................. 63-242062

[51] Int. Cl.$^5$ .............................. C08G 77/06
[52] U.S. Cl. ..................... 528/15; 525/474;
525/476; 525/479; 528/31; 528/27; 528/28;
556/425; 556/467; 556/479
[58] Field of Search ........... 528/27, 28, 15, 31;
556/479, 467, 425; 525/476, 479, 474

[56] References Cited

U.S. PATENT DOCUMENTS 4,680,366  7/1987  Tanaka et al. .................. 528/27
4,929,051  5/1990  Rogler et al. .................... 428/383

Primary Examiner—Melvyn I. Marquis
Attorney, Agent, or Firm—Wyatt, Gerber, Burke & Badie

[57] ABSTRACT

The invention provides a diorganopolysiloxane having a hydroxy- and amino-functional reactive group bonded only to one of the terminal silicon atoms of the linear molecular chain ends. The diorganopolysiloxane compound, which is useful as a modifying agent of various kinds of synthetic resins, is represented by the general formula

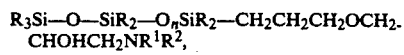

in which R is a monovalent hydrocarbon group, $R^1$ and $R^2$ are each a hydrogen atom or a monovalent hydrocarbon group selected from the class consisting of alkyl groups having 1 to 18 carbon atoms and aryl groups having 6 to 15 carbon atoms, at least one of $R^1$ and $R^2$ being not a hydrogen atom, or $R^1$ and $R^2$ are each a divalent group jointly forming a morpholino group together with the nitgoren atom and the subscript n is zero or a positive integer not exceeding 1000.

7 Claims, No Drawings

ONE END-REACTIVE ORGANOPOLYSILOXANE COMPOUND

BACKGROUND OF THE INVENTION

The present invention relates to a novel organopolysiloxane compound having a reactive group bonded to the silicon atom only at one of the molecular chain ends. More particularly, the invention relates to such a novel organopolysiloxane compound useful as a modifying agent of various kinds of synthetic resins by utilizing the reaction with the reactive group at the molecular chain end of the organopolysiloxane. The invention also relates to a method for the preparation of such a novel organopolysiloxane compound.

There are known various organopolysiloxane compounds having a hydroxy-functional or amino-functional substituent group bonded to the silicon atom in the molecule. In the organopolysiloxane compounds of this type known in the prior art, the hydroxy- or amino-functional reactive groups are bonded to both of the terminal silicon atoms in the molecular chain or to the silicon atoms at random positions in the molecular chain excepting the terminal ones.

Such a reactive organopolysiloxane compound is reactive at the amino- or hydroxy-functional reactive groups with various kinds of monomeric compounds having an acid anhydride structure, carboxyl group, isocyanato group, epoxy group and the like in the molecule, from which polyimide resins, polyamide resins, polyurethane resins, epoxy resins and the like are prepared, and is widely used as a modifying agent of these synthetic resins which introduces the organopolysiloxane structure into the synthetic resin thereby to improve the characteristics of the resin such as thermal properties, interfacial properties, gas permeability and the like inherently characteristic in organopolysiloxanes.

The attempt of modification of a synthetic resin by using the above mentioned reactive organopolysiloxane compound sometimes encounters a serious problem as a consequence of the fact that the organopolysiloxane compound has a plural number of the reactive groups bonded to the silicon atoms in a molecule, especially, when the organopolysiloxane has three or more of the reactive groups in a molecule since such a compound acts as a crosslinking agent to cause gelation of the polymer to be modified therewith in addition to the relatively low effect of modification of synthetic resins even by setting aside the problem that this technique of modification is applicable to limited kinds of synthetic resins. Therefore, it is eagerly desired to develop a novel reactive organopolysiloxane compound which can be used in the modification reaction of synthetic resins without the above described problems and disadvantages in the reactive organopolysiloxane compounds in the prior art.

SUMMARY OF THE INVENTION

The organopolysiloxane compound of the invention is a novel compound not known in the prior art nor described in any literatures and is characterized in that the organopolysiloxane molecule has one and only one reactive group bonded to one of the silicon atoms at the molecular chain ends.

Thus, the organopolysiloxane compound of the invention is represented by the general formula $$R_3Si-O-SiR_2-O)_nSiR_2-CH_2CH_2CH_2OCH_2CHOHCH_2NR^1R^2, \quad (I)$$

in which R is a monovalent hydrocarbon group, $R^1$ and $R^2$ are each a hydrogen atom or a monovalent hydrocarbon group selected from the class consisting of alkyl groups having 1 to 18 carbon atoms and aryl groups having 6 to 15 carbon atoms, provided that $R^1$ and $R^2$ may not both be hydrogen on the same molecule of the compound, or, alternatively, $R^1$ and $R^2$ are each a divalent group jointly forming the ring structure of a morpholino group together with the nitrogen atom and the subscript n is zero or a positive integer not exceeding 1000.

The above defined organopolysiloxane compound can be prepared in a method comprising the successive steps of:

(a) reacting allyl glycidyl ether with an SiH-containing organopolysiloxane of the formula $$R_3Si-O-SiR_2-O)_nSiR_2-H, \quad (II)$$

in which R and n each have the same meaning as defined above, to give a 3-glycidyloxypropyl-containing organopolysiloxane of the formula $$R_3Si-O-SiR_2-O)_nSiR_2-CH_2CH_2CH_2OG, \quad (III)$$

in which G is a glycidyl group and R and n each have the same meaning as defined above, and (b) reacting the above obtained glycidyloxy-containing organopolysiloxane with a substituted amine of the formula $$R^1R^2NH, \quad (IV)$$

in which $R^1$ and $R^2$ each have the same meaning as defined above.

DETAILED DESCRIPTION OF THE PREFERRED EMBODIMENTS

Different from conventional reactive organopolysiloxane compounds having a plural number of reactive groups in a molecule, the above defined one end-reactive organopolysiloxane compound of the invention is useful with versatility as a modifying agent of various kinds of synthetic resins without the disadvantage of gelation of the modified resin by cross-linking because the organopolysiloxane moiety is bonded to the synthetic resin only at one molecular chain end, the other molecular chain end being unbonded, without being immobilizably bound to form a network structure.

In the general formula (I) representing the one end-reactive organopolysiloxane compound of the invention, the group denoted by R is a monovalent hydrocarbon group such as alkyl groups, e.g., methyl and ethyl groups, and aryl groups, e.g., phenyl group. R is typically a methyl group. The compound is characterized by the reactive group, i.e. 3-[2-hydroxy-3-(N-substituted amino)propyloxy]propyl group, bonded to one of the terminal silicon atoms. The other end of the polysiloxane chain is blocked with a trimethyl silyl group. When the subscript n is zero, the compound is pentamethyl 3-[2-hydroxy-3-(N-substituted amino)propyloxy]propyl disiloxane. The N-substituting groups denoted by $R^1$ and $R^2$ are each a hydrogen atom or a monovalent hydrocarbon group selected from the class consiting of alkyl groups having 1 to 18 carbon atoms, e.g., methyl, ethyl, n-propyl and isopropyl groups, and aryl groups having 6 to 15 carbon atoms, e.g., phenyl group, provided that $R^1$ and $R^2$ may not both be hydrogen on the same molecule of the compound. Needless to say, $R^1$ and $R^2$ are not necessarily of the same kind of the hydrocarbon groups. Alternatively, $R^1$ and $R^2$ are each a divalent group jointly forming a ring structure such as a morpholino group together with the nitrogen atom. An example of the reactive group is 3-[(2-hydroxy-3-isopropylaminopropyl)oxy]propyl group of the formula —$CH_2CH_2CH_2OCH_2CHOHCH_2NHCH(CH_3)_2$. The subscript n can be a positive integer up to 1000 but, when the intended application of the organopolysiloxane is as a modifying agent of a synthetic resin, the value of n is preferably 200 or smaller in respect of the compatibility and reactivity with the moiety of the synthetic resin.

The above described one end-reactive organopolysiloxane can be synthesized from an organopolysiloxane, e.g., polydimethylsiloxane, having a hydrogen atom directly bonded to one of the silicon atoms at the molecular chain ends and represented by the general formula (II) given above, referred to as a one end-SiH organopolysiloxane hereinbelow, as one of the starting reactants. Thus, the one end-SiH organopolysiloxane of the formula (II) is first reacted with allyl glycidyl ether to give the 3-glycidyloxypropyl-terminated organopolysiloxane of the general formula (III) as the product of the hydrosilation reaction, which is then reacted with the substituted amine compound of the general formula (IV) given above.

The one end-SiH organopolysiloxane of the formula (II) is a known compound and can be prepared, for example, in a procedure described in Japanese Patent Publication Nos. 42-11061 and 45-1070 by conducting a living polymerization of hexamethyl cyclotrisiloxane in the presence of lithium trimethyl silanolate or a combination of trimethyl silanol and a pentacoordination compound of silicon. The hydrosilation reaction between the one end-SiH organopolysiloxane and allyl glycidyl ether is performed usually in the presence of a catalytic amount of a compound of a metal belonging to the VIIIth Group of the Periodic Table, e.g., platinum, such as chloroplatinic acid dissolved in an alcohol as a catalyst by using an excessive amount, e.g., 1.2 times by moles or larger, of allyl glycidyl ether relative to the one end-SiH organopolysiloxane. The hydrosilation reaction is complete usually within 1 to 8 hours when the reaction temperature is 80° to 120° C. to give the 3-glycidyloxypropyl terminated organopolysiloxane of the general formula (III) such as pentamethyl 3-glycidyloxypropyl disiloxane, $\alpha$-methyl-$\omega$-(3-glycidyloxypropyl) poly(dimethyl siloxane) and the like.

The thus obtained 3-glycidyloxypropyl-terminated organopolysiloxane of the general formula (III) is then reacted with the substituted amine compound of the general formula (IV) which is exemplified by methyl amine, ethyl amine, propyl amine, isopropyl amine, butyl amine, isobutyl amine, octyl amine, dimethyl amine, diethyl amine, dipropyl amine, dibutyl amine, diethanol amine, morpholine and the like. This reaction proceeds by heating a mixture of the glycidyl-containing organopolysiloxane and an excessive amount or, for example, 1.2 to 4.0 moles of the amine compound per mole of the organopolysiloxane at a temperature of 50° to 120° C. for 2 to 24 hours.

The one end-reactive organopolysiloxane of the invention is reactive with other monomeric compounds when the monomeric compound has a structure of acid anhydride, carboxyl group, isocyanate group, epoxy group and the like having reactivity with the hydroxy and/or amino groups. Therefore, polymerization of the thus modified monomeric compound gives a polymeric product imparted with the unique properties inherent in organopolysiloxanes. Namely, the organopolysiloxane compound of the invention is useful as a modifying agent of various kinds of synthetic resins such as polyimide resins, polyamide resins, polyurethane resins, epoxy resins and the like when it is desired that these synthetic resins are improved or modified in respect of the impact strength, flexibility, heat and cold resistance, wearing resistance, water repellency, lubricity, electric properties and the like. By virtue of the polar nature of the molecule, the organopolysiloxane compound of the invention is expected to be a starting material in the preparation of certain surface active agents.

In the following, the inventive organopolysiloxane compound and the method for the preparation thereof are described in more detail by way of examples including the description of the preparation and characterization of the compound.

Example 1

Pentamethyl 3-[(2-hydroxy-3-N-isopropylamino)-propyloxy]-propyl disiloxane was prepared in the following manner.

In the first place, 273.6 g (2.4 moles) of allyl glycidyl ether and 0.4 ml of a solution prepared by dissolving 1 g of chloroplatinic acid in 50 ml of isopropyl alcohol were introduced into a flask of 1 liter capacity and the mixture was heated at 70° C. Then, 296 g (2.0 moles) of pentamethyl disiloxane were added thereto dropwise over a period of 30 minutes and the reaction mixture was kept at 90° C. for additional 1 hour to complete the reaction. The reaction mixture thus obtained was subjected to distillation under reduced pressure to give 399 g of a clear and colorless liquid fraction boiling at 118° to 121° C. under a pressure of 12 mmHg and having a viscosity of 3.1 centistokes at 25° C., specific gravity of 0.915 at 25° C., refractive index of 1.4258 at 25° C. and epoxy equivalent of 265 g/mole, of which the gas chromatographic purity was 97.4%. This product could be identified to be pentamethyl 3-glycidyloxypropyl disiloxane from the results of the NMR, infrared absorption spectrophotometric and mass spectrometric analyses shown below. The above mentioned yield was 76.1% of the theoretical value.

$^1$H-NMR (CDCl$_3$): $\delta$ (ppm)
0.1 (Si—CH$_3$, s, 15H)
0.5 (Si—CH$_2$, m, 2H)
1.7 (—CH$_2$—, m, 2H)

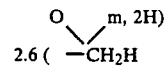
2.6 ( —CH$_2$H

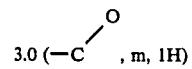
3.0 (—C     , m, 1H)

3.2 to 3.5 (—CH$_2$—O, m, 4H)
Infrared absorption spectrum: $\nu_{max}$
3050 cm$^{-1}$ (—CH$_2$— in epoxy)
2960 cm$^{-1}$ (C—H)
1260 cm$^{-1}$ (Si—CH$_3$)
1120 to 1050 cm$^{-1}$ (Si—O)
Mass spectrometry

| -continued |
| --- |
| m/e: 262 (molecular ion peak) |

Into a flask of 1 liter capacity were introduced 262 g (1.0 mole) of the pentamethyl 3-glycidyloxypropyl disiloxane obtained above, 70.8 g (1.2 moles) of isopropyl amine and 200 g of toluene and the mixture in the flask was heated under reflux for 16 hours to effect the reaction. The temperature of the reaction mixture in the flask, which was 80° C. at the beginning of the reaction, was increased to 110° C. at the end of the above mentioned reaction time. The reaction mixture thus obtained was subjected to distillation under reduced pressure to give 169 g of a clear and light yellow liquid fraction boiling at 139° to 140° C. under a pressure of 4 mmHg and having a viscosity of 34.4 centistokes at 25° C., specific gravity of 0.910 at 25° C., refractive index of 1.4378 at 25° C. and amine equivalent of 326 g/mole, of which the gas chromatographic purity was 99.3%. This product could be identified to be pentamethyl 3-[(2-hydroxy-3-N-isopropylamino)propyloxy]propyl disiloxane from the results of the NMR, infrared absorption spectrophotometric and mass spectrometric analyses shown below. The above mentioned yield was 52.6% of the theoretical value.

| $^1$H-NMR (CDCl$_3$) : δ (ppm) |
| --- |
| 0.1 (Si—CH$_3$, s, 15H) |
| 0.5 (Si—CH$_2$, m, 2H) |
| 1.0 to 1.1 [C(CH$_3$)$_2$:, d, 6H] |
| 1.7 (—CH$_2$—, m, 2H) |
| 2.7 (—CH$_2$—NH—CH, m, 4H) |
| 3.4 (—O—CH$_2$, C—OH, m, 5H) |
| 3.8 (>CH—, m, 1H) |
| Infrared absorption spectrum : ν$_{max}$ |
| 300 cm$^{-1}$ (O—H) |
| 960 cm$^{-1}$ (C—H) |
| 260 cm$^{-1}$ (Si—CH$_3$) |
| 120 to 1050 cm$^{-1}$ (Si—O) |
| Mass spectrometry |
| m/e : 321 (molecular ion peak) |

Example 2

An α-[3-(2-hydroxy-3-N-isopropylamino)propyloxy]propyl-ω-methyl poly(dimethyl siloxane) was prepared in the following manner.

Thus, 1640 g (0.91 mole) of a one end-SiH dimethyl polysiloxane expressed by the formula Me$_3$Si—O—SiMe$_2$—O)$_n$SiMe$_2$—H, in which n is about 23 on an average and Me is a methyl group, of which the volume of hydrogen gas evolution by alkali decomposition was 12.4 ml/g corresponding to a number-average molecular weight of 1810, 1100 g of toluene and 0.7 ml of the same isopropyl alcohol solution of chloroplatinic acid as used in Example 1 were introduced into a flask of 5 liter capacity and the mixture was heated and kept at 100° C. Then, 114 g (1.0 mole) of allyl glycidyl ether were added dropwise into the mixture in the flask over a period of 1 hour and agitation of the mixture was continued for additional 3 hours under reflux to complete the reaction.

Thereafter, the reaction mixture was subjected to the test for the hydrogen gas evolution by alkali decomposition to confirm complete disappearance of the SiH groups in the starting one end-SiH organopolysiloxane followed by stripping of the solvent and the unreacted starting material boiling at a relatively low temperature for 2 hours under a pressure of 2 mmHg at 130° C. to give 1660 g of a liquid product.

The thus obtained product was a clear and light yellow liquid having a viscosity of 28.4 centistokes at 25° C., specific gravity of 0.970 at 25° C., refractive index of 1.4064 at 25° C. and epoxy equivalent of 2140 g/mole and could be identified from the results of the NMR, infrared absorption spectrophotometric and gel permeation chromatographic analyses shown below to be α-(3-glycidyloxypropyl)-ω-methyl dimethyl polysiloxane expressed by the following formula:

Me$_3$Si—O—SiMe$_2$—O)$_n$SiMe$_2$—CH$_2$CH$_2$CH$_2$—O—G, in which each symbol has the same meaning as defined above. The above mentioned yield was 52.6% of the theoretical value.

| $^1$H-NMR (CDCl$_3$): δ (ppm) |  |
| --- | --- |
| 0.8 (—CH$_2$—, m, 2H) |  |
| 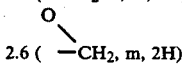 2.6 ( —CH$_2$, m, 2H) |  |
| 3.2 to 3.5 (—CH$_2$—O, —CH—O—, m, 5H) |  |
| Infrared absorption spectrum: ν$_{max}$ |  |
| 3050 cm$^{-1}$ (—CH$_2$— in epoxy) |  |
| 2960 cm$^{-1}$ (C—H) |  |
| 1260 cm$^{-1}$ (Si—CH$_3$) |  |
| 1120 to 1050 cm$^{-1}$ (Si—O) |  |
| Gel permeation chromatography |  |
| Number-average molecular weight (M$_n$) | 2200 |
| Weight-average molecular weight (M$_w$) | 3100 |
| (with reference to polystyrenes) |  |
| Degree of polydispersion M$_w$/M$_n$ = 1.4 |  |

In the next place, 857 g (about 0.4 mole) of the above obtained 3-glycidyloxypropyl-terminated dimethyl polysiloxane, 480 g of isopropyl alcohol and 24.8 g (0.41 mole) of isopropyl amine were introduced into a flask of 2 liter capacity and the mixture in the flask was heated under reflux for 4 hours. The thus obtained reaction mixture was subjected to stripping of the solvent and the unreacted reactants of low boiling point for 2 hours at 110° C. under a pressure of 2 mmHg and then 4 g of active carbon were added thereto and agitated for 2 hours at room temperature followed by filtration to remove the active carbon to give 855 g of a clear and light yellow liquid having a viscosity of 70.6 centistokes at 25° C., specific gravity of 0.970 at 25° C., refractive index of 1.4088 at 25° C. and amine equivalent of 2280 g/mole. This product could be identified from the results of the NMR, infrared absorption spectrophotometric and gel permeation chromatographic analyses shown below to be an α-[3-(2hydroxy-3-N-isopropylamino)propyloxy]propyl ω-methyl poly(dimethyl siloxane) expressed by the formula Me$_3$Si—O—SiMe$_2$—O)$_n$SiMe$_2$—CH$_2$CH$_2$CH$_2$—O—CH$_2$CHOHCH$_2$NHCH(CH$_3$)$_2$, in which n and Me each have the same meaning as defined above. The above mentioned yield of the product was 97% of the theoretical value.

| $^1$H—NMR (CDCl$_3$) : δ (ppm) | |
|---|---|
| 0.1 (Si—CH$_3$, s, 15H) | |
| 0.5 (Si—CH$_2$, m, 2H) | |
| 1.0–1.1 (C(CH$_2$)$_2$, d, 6H) | |
| 1.7 (—CH$_2$, m, 2H) | |
| 2.7 (—CH$_2$—NH—CH, m, 4H) | |
| 3.4 (—O—CH$_2$, C—OH, m, 5H) | |
| 3.8 (>CH—, m, 1H) | |
| Infrared absorption spectrum : ν$_{max}$ | |
| 3300 cm$^{-1}$ (O—H) | |
| 2960 cm$^{-1}$ (C—H) | |
| 1260 cm$^{-1}$ (Si—CH$_3$) | |
| 1120 to 1050 cm$^{-1}$ (Si—O) | |
| Gel permeation chromatography | |
| Number-average molecular weight (M$_n$) | 2300 |
| Weight-average molecular weight (M$_w$) | 3400 |
| (with reference to polystyrenes) | |
| Degree of polydispersion M$_w$/M$_n$ = 1.5 | |

Example 3

In a manner similar to Example 2, an α-(3-glycidyloxypropyl) ω-methyl poly(dimethyl siloxane) expressed by the formula $$Me_3Si—O—SiMe_2—O)_mSiMe_2—CH_2CH_2CH_2—O—G,$$

in which m is about 18 on an average and G and Me each have the same as defined above, was prepared and 256 g (0.16 mole) of the same were dissolved in 155 g of isopropyl alcohol together with 16.8 g (0.23 mole) of diethyl amine. The mixture was heated for 4 hours under reflux to effect the reaction of the amine compound and the epoxy groups. After completion of the reaction, the reaction mixture was processed in the same manner as in Example 2 to give 234 g of a clear and light yellow liquid product having a viscosity of 25.4 centistokes at 25° C., specific gravity of 0.959 at 25° C., refractive index of 1.4102 at 25° C. and amine equivalent of 1670 g/mole, which could be identified from the results of the NMR, infrared absorption spectrophotometric and gel permeation chromatographic analyses indicated below to be an α-3-[(2-hydroxy-3-diethylamino propyloxy) propyl] ω-methyl poly(dimethyl siloxane) expressed by the formula $$Me_3Si—O—SiMe_2—O)_mSiMe_2—CH_2CH_2CH_2—O—CH_2CHOHCH_2NEt_2,$$

in which m and Me each have the same meaning as defined above and Et is an ethyl group. The above mentioned yield was 87% of the theoretical value.

| $^1$H—NMR (CDCl$_3$) : δ (ppm) | |
|---|---|
| 1.0 (NCH$_2$ CH$_3$, t, 6H) | |
| 1.2 to 1.6 (SiCH$_2$CH$_2$, m, 2H) | |
| 2.3 to 3.0 (NCH$_2$, m, 6H) | |
| 3.2 to 3.8 (OCH$_2$, OCH, m, 5H) | |
| Infrared absorption spectrum : ν$_{max}$ | |
| 3300 cm$^{-1}$ (O—H) | |
| 2960 cm$^{-1}$ (C—H) | |
| 1260 cm$^{-1}$ (Si—CH$_3$) | |
| 1090 cm$^{-1}$ (Si—O) | |
| Gel permeation chromatography | |
| Number-average molecular weight (M$_n$) | 2800 |
| Weight-average molecular weight (M$_w$) | 3200 |
| (with reference to polystyrenes) | |
| Degree of polydispersion M$_w$/M$_n$ = 1.1 | |

Example 4

A reaction mixture was prepared by dissolving 285 g (0.18 mole) of the same 3-glycidyloxypropyl-terminated poly(dimethyl siloxane) as used in Example 3 and 23.5 g (0.27 mole) of morpholine in 162 g of isopropyl alcohol and heated under reflux for 4 hours to effect the reaction of the morpholine and the epoxy groups. After completion of the reaction, the reaction mixture was processed in the same manner as in Example 2 to give 269 g of a clear and light yellow liquid product having a viscosity of 35.1 centistokes at 25° C., specific gravity of 0.975 at 25° C., refractive index of 1.4138 at 25° C. and amine equivalent of 1640 g/mole, which could be identified from the results of the NMR, infrared absorption spectrophotometric and gel permeation chromatographic analyses indicated below to be an α-3-[(2-hydroxy-3-N-morpholino propyloxy) propyl] ω-methyl poly(dimethyl siloxane) expressed by the formula $$Me_3Si—O—SiMe_2—O)_mSiMe_2—CH_2CH_2CH_2—O—CH_2CHOHCH_2—Mp,$$

in which m and Me each have the same meaning as defined above and Mp is an N-morpohilino group. The above mentioned yield was 90% of the theoretical value.

| $^1$H—NMR (CDCl$_3$) : δ (ppm) | |
|---|---|
| 0.4 to 0.7 (SiCH$_2$, m, 2H) | |
| 1.3 to 1.8 (SiCH$_2$CH$_2$, m, 2H) | |
| 2.3 to 2.6 (NCH$_2$, m, 6H) | |
| 3.2 to 3.8 (—CH$_2$—O, O—CH, m, 9H) | |
| Infrared absorption spectrum : ν$_{max}$ | |
| 3300 cm$^{-1}$ (O—H) | |
| 2960 cm$^{-1}$ (C—H) | |
| 1260 cm$^{-1}$ (Si—CH$_3$) | |
| 1020 cm$^{-1}$ (Si—O) | |
| Gel permeation chromatography | |
| Number-average molecular weight (M$_n$) | 2800 |
| Weight-average molecular weight (M$_w$) | 3000 |
| (with reference to polystyrenes) | |
| Degree of polydispersion M$_w$/M$_n$ = 1.1 | |

What is claimed is:

1. An organopolysiloxane compound represented by the general formula $$R_3Si—O—SiR_2—O)_nSiR_2—CH_2CH_2CH_2OCH_2CHOHCH_2NR^1R^2,$$

in which R is a monovalent hydrocarbon group, $R^1$ and $R^2$ are each a hydrogen atom or a monovalent hydrocarbon group selected from the class consisting of alkyl groups having 1 to 18 carbon atoms and aryl groups having 6 to 15 carbon atoms, provided that $R^1$ and $R^2$ may not both be hydrogen on the same molecule of the compound, or $R^1$ and $R^2$ are each a divalent group jointly forming the ring structure of a morpholino group together with the nitrogen atom and the subscript n is zero or a positive integer not exceeding 1000.

2. The organopolysiloxane compound as claimed in claim 1 wherein the group denoted by R is a methyl group.

3. The organopolysiloxane compound as claimed in claim 1 wherein the group denoted by $R^1$ is an isopropyl group and the group denoted by $R^2$ is a hydrogen atom.

4. The organopolysiloxane compound as claimed in claim 1 wherein the groups denoted by $R^1$ and $R^2$ are each an ethyl group.

5. The organopolysiloxane compound as claimed in claim 1 wherein the groups denoted by $R^1$ and $R^2$ are each a divalent group forming a morpholino group together with the nitrogen atom.

6. The organopolysiloxane compound as claimed in claim 1 wherein the subscript n is a positive integer not exceeding 200.

7. A method for the preparation of an organopolysiloxane compound represented by the general formula $$R_3Si\!-\!O\!-\!SiR_2\!-\!O)_nSiR_2\!-\!CH_2CH_2CH_2OCH_2\text{-}CHOHCH_2NR^1R^2,$$

in which R is a monovalent hydrocarbon group, $R^1$ and $R^2$ are each a hydrogen atom or a monovalent hydrocarbon group selected from the class consisting of alkyl groups having 1 to 18 carbon atoms and aryl groups having 6 to 15 carbon atoms, provided that $R^1$ and $R^2$ may not both be hydrogen on the same molecule of the compound, or $R^1$ and $R^2$ are each a divalent group jointly forming the ring structure of a morpholino group together with the nitrogen atom and the subscript n is zero or a positive integer not exceeding 1000, which comprises the steps of:

(a) reacting allyl glycidyl either with an SiH-containing organopolysiloxane of the formula $$R_3Si\!-\!O\!-\!SiR_2O)_nSiR_2\!-\!H,$$

in which R and n each have the same meaning as defined above, to produce a 3-glycidyloxypropyl-containing organopolysiloxane of the formula $$R_3Si\!-\!O\!-\!SiR_2\!-\!O)_nSiR_2\!-\!CH_2CH_2CH_2OG,$$

in which G is a glycidyl group and R and n each have the same meaning as defined above, in the presence of a platinum compound as a catalyst; and (b) reacting the above obtained 3-glycidyloxypropyl-containing organopolysiloxane with an amine compound represented by the general formula $$R^1R^2NH,$$

in which $R^1$ and $R^2$ each have the same meaning as defined above.

* * * * *